United States Patent [19]

King

[11] Patent Number: 4,630,611

[45] Date of Patent: Dec. 23, 1986

[54] ORTHOGONALLY-SENSING LEAD

[75] Inventor: Wendell L. King, North Oaks, Minn.

[73] Assignee: Medtronic, Inc., Minneapolis, Minn.

[21] Appl. No.: 230,572

[22] Filed: Feb. 2, 1981

[51] Int. Cl.[4] ............................................... A61B 5/04
[52] U.S. Cl. ................................ 128/642; 128/419 P; 128/786
[58] Field of Search .................... 128/639, 642, 419 P, 128/419 D, 784, 785, 786, 699

[56] References Cited

U.S. PATENT DOCUMENTS

| | | | |
|---|---|---|---|
| 3,326,207 | 6/1967 | Egan | 128/642 |
| 3,548,813 | 12/1970 | Berner | 128/2.06 |
| 3,572,344 | 3/1971 | Bolduc | 128/786 |
| 3,710,174 | 1/1973 | Cerniglia, Jr. | 315/22 |
| 3,865,118 | 2/1975 | Bures | 128/404 |
| 3,937,226 | 2/1976 | Funke | 128/419 D |
| 3,983,867 | 10/1976 | Case | 128/2.06 G |
| 4,164,939 | 8/1979 | Kolin | 128/692 |
| 4,172,451 | 10/1979 | Kline | 128/642 |
| 4,198,963 | 4/1980 | Barkalow et al. | 128/642 |
| 4,216,780 | 8/1980 | Rubel et al. | 128/699 |
| 4,236,525 | 12/1980 | Sluetz et al. | 128/419 |
| 4,289,138 | 9/1981 | Halvorsen | 128/642 |
| 4,354,497 | 10/1982 | Kahn | 128/419 D |
| 4,365,639 | 12/1982 | Goldreyer | 128/786 |

FOREIGN PATENT DOCUMENTS 0009732 4/1980 European Pat. Off. .

OTHER PUBLICATIONS

"Engineering Aspects of Implantable Cardiac Pacemarkers", by Peter P. Tarjan, Ph.D., published in *Cardiac Pacing*, P. Samet Editor, New York 1973, pp. 47-71.

"A Comparison of Unipolar and Bipolar Electrograms for Cardiac Pacemaker Sensing", by DeCaprio et al., published in *Circulation*, vol. 56, No. 5, Nov. 1977, pp. 750-755.

Abstract entitled "Proposed Cardiac Pacemaker System Combining Unipolar Stimulation With Bipolar Sensing", by Hurzeler et al., published in *IEEE Transactions on Biomedical Engineering*, vol. BME-26, No. 7, Jul. 1979.

"Conduction Cardiograph-Bundle of His Detector", published in *IEEE Transactions on Biomedical Engineering*, vol. BME-22, pp. 269-274, Jul. 1975, by Louis Siegel, et al.

*Primary Examiner*—William E. Kamm
*Attorney, Agent, or Firm*—Reed A. Duthler; Joseph F. Breimayer; John L. Rooney

[57] ABSTRACT

A body implantable lead having multiple spatially displaced electrodes to facilitate the sensing of current vectors in muscle tissue. The lead employs three mutually orthogonal electrode pairs. Each electrode pair is capable of measuring current vectors within the muscle tissue in a different one of three mutually orthogonal directions. All six electrodes are mounted about a single cylindrical lead body. Each of the six electrodes is coupled to an in-line electrical connector at a proximal end of the sensing lead. Because the electrodes are relatively closely spaced on a convenient size lead, being of about 8-14 French in diameter, state of the art processing techniques are required to resolve the direction of current flow within the heart muscle.

4 Claims, 5 Drawing Figures

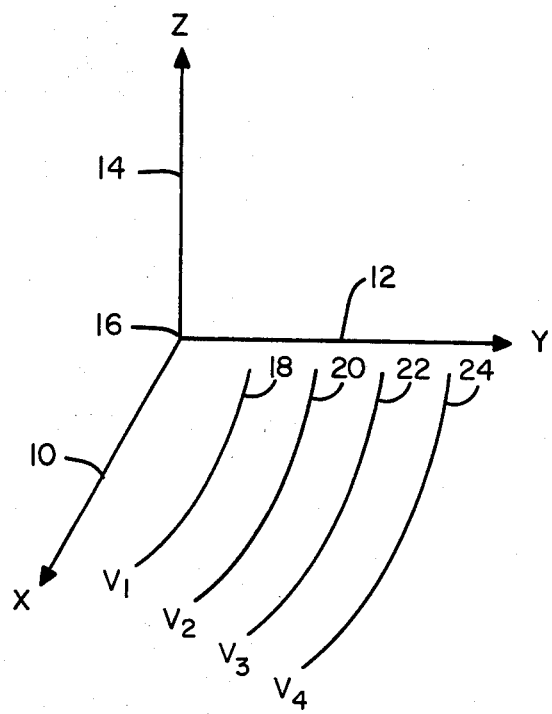
Fig. 1
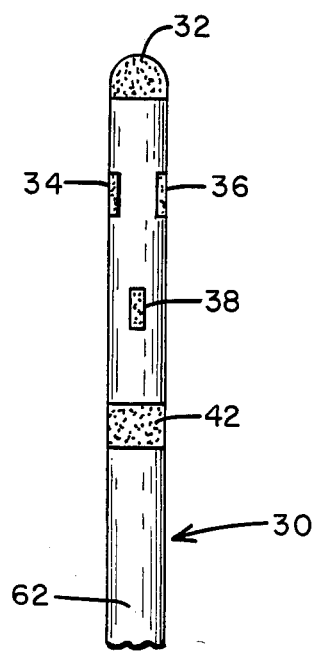
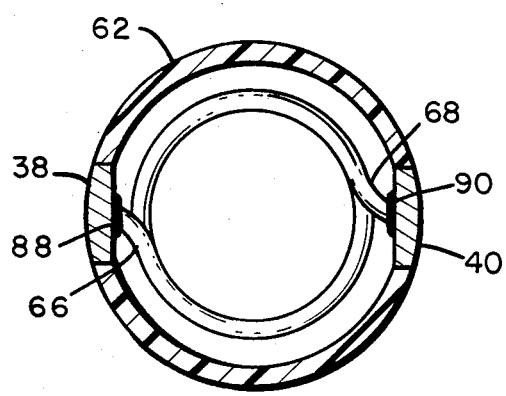
Fig. 5
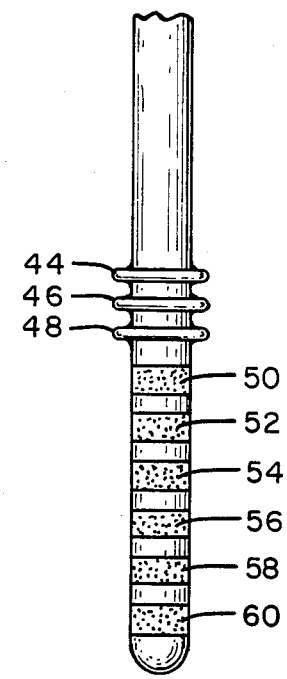
Fig. 2

U.S. Patent   Dec. 23, 1986   Sheet 2 of 2   4,630,611
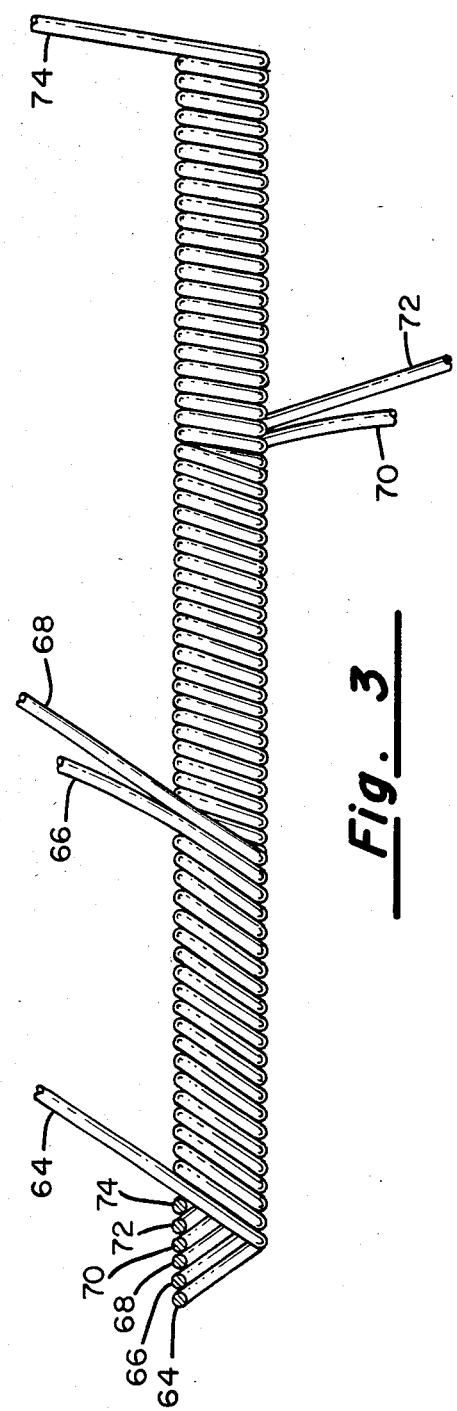
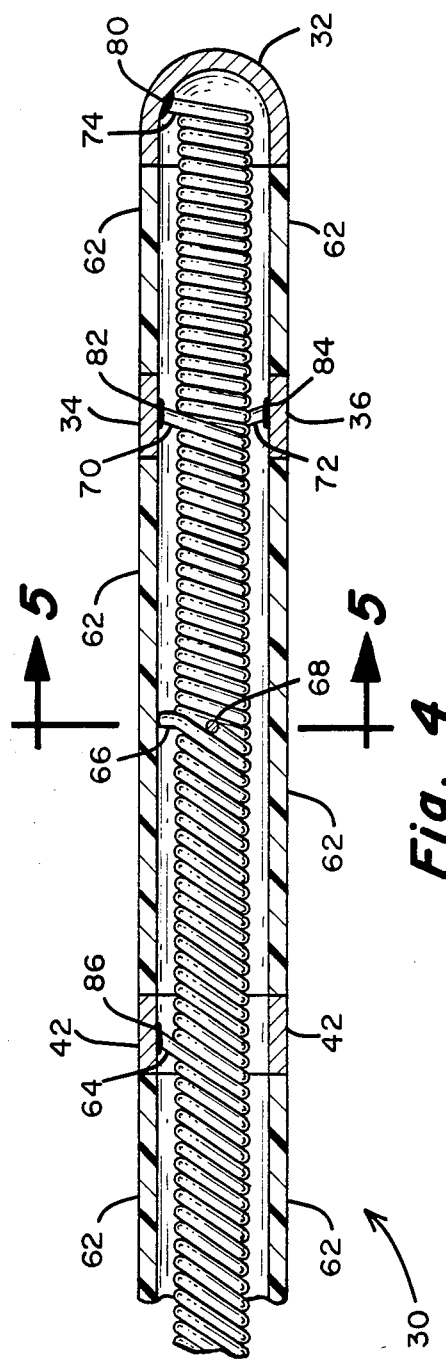

ORTHOGONALLY-SENSING LEAD

BACKGROUND OF THE INVENTION

1. Field of the Invention

The present invention relates generally to implantable medical devices, and more specifically relates to electrical sensing leads for medical applications.

2. Description of the Prior Art

A number of inventors have taught systems which have multiply displaced electrodes. Typically, these electrodes are used for both stimulation and sensing. However, notwithstanding the displacement of multiple electrodes, these references appear not to teach displacing electrodes about three mutually orthogonal axes for the purposes of measuring current vectors in three dimensional space. U.S. Pat. No. 4,154,247 issued to O'Neill, teaches the use of multiply spaced electrodes. FIG. 4f, for example, teaches the use of three electrodes. However, it is assumed from the teaching of O'Neill that the embodiment pictured in FIG. 4f uses electrodes 612 and 615 connected to a single conductor, making them electrically equivalent. The result is simply a bipolar lead with the sensing capability located within a plane rather than in a line as with most bipolar leads.

The European Patent Office Publication No. 0,009,734 issued to Babotai discloses a lead having electrodes dispersed over more than one axis. As with the teaching of O'Neill these electrodes are directed primarily to stimulation rather than sensing. Furthermore, because the electrodes do not emanate from a single cylindrical lead body, the exact positional representation of currents sensed by these electrodes is extremely difficult to determine.

SUMMARY OF THE INVENTION

The present invention is directed toward sensing current vectors within the muscle tissue. It is deemed important to sense the current vectors in three dimensional space since certain types of arrythmias are preceded by changes of direction of current vectors without corresponding changes in their scalar value. The three pairs of electrodes used are mounted along a single cylindrical lead body. Mounting all six electrodes about the same cylindrical body enables much more accurate assumptions about the spatial relations of these electrodes after implant.

Each of the six electrodes is cabled to a separate one of six conductors which run the length of the lead body. The most distal electrode is found at the distal tip of the lead. The most proximal electrode is a ring electrode going about the entire circumference of the lead body. Measurements between the most proximal and most distal electrode measure the current vectors in the direction of lead body. Intermediate the most proximal and distal electrodes are two electrode pairs. Each electrode of each electrode pair is located equidistant from the distal tip of the electrode. Each electrode of a pair is spaced 180° from its corresponding electrode. The two electrode pairs are spaced at 90° with reference to the axis of the main body of the lead.

Current vectors may be thus measured between electrode pairs providing a representation of current flow within three dimensional space. Because the distance between the electrode pairs is very small (on the order of a few millimeters), rapid processing of the sensed signals is required to produce a signal representative of a current vector in three dimensional space. It is felt that such processing capability is easily within the realm of the current implant technology.

The exact implant location of the lead will determine the relationship between the current vectors sensed and inertial space. Determining this exact position would be extremely difficult under practical circumstances, however, fortunately it appears that this is not necessary for the sensing of the arrhythmias of concern. It is apparent that the main purpose of the sensing process is to determine abnormal changes in direction of the sensed current vectors.

However, exact placement of the lead may be performed using three-dimensional radiography or tomography when desirable for diagnostic purposes.

BRIEF DESCRIPTION OF THE DRAWINGS

FIG. 1 is a schematic representation of electrical signals within muscle tissue as shown in the three dimensional space.

FIG. 2 is a plan view of a sensing lead employing the present invention.

FIG. 3 shows a view of the six conductor coil used within the main body of the lead.

FIG. 4 is a cross sectional view of the distal end of the sensing lead showing electrode placement and coupling to the various conductors of the lead body.

FIG. 5 is a cross sectional view of the lead body showing the construction of electrodes 38 and 40.

BRIEF DESCRIPTION OF THE PREFERRED EMBODIMENTS

The present invention is described as embodied in a sensing lead having six electrodes arranged as three electrodes pairs about a single cylindrical lead body. It will be apparent to those of ordinary skill in the art that different configurations of electrodes are encompassed within the present teaching. It is further assumed that those of ordinary skill in the art will appreciate the application of stimulation electrodes along with the presence of sensing electrodes about the same lead body or the use of certain electrodes for both sensing and stimulation as is common in the art.

FIG. 1 is a schematic diagram of polarization currents within muscle tissue as represented in three dimensional space. The purpose of this schematic representation is to illustrate the results of random placement of electrode pairs in relation to measuring the current shown. The current is represented by wave front V1, reference 18; V2, reference 20; V3, reference 22; and V4, reference 24. Each of these wave fronts corresponds to a line of equal potential. For the purposes of this example assume that the potential of V1, reference 18 is less than that of the potential of V2, reference 20; which is less than that of V3, reference 22; which is greater than that of V4, reference 24. Notice that this current flow is represented only within the plane created by X axis 10 and Y axis 12. There is no current flow within the direction of the Z axis 14.

Let us now assume that an electrode pair is inserted into the three dimensional space represented by X axis 10, Y axis 12 and Z axis 14. If these two electrodes are displaced along Z axis 14 for example, notice that no current will be sensed (except at Z=0). Notice also that a pair of electrodes displaced along X axis 10 will also not sense any potential difference with the current flow as shown. Only an electrode pair having a nonzero length projection along Y axis 12 will be able to sense the current flow shown. In normal practice with chronically implanted leads, only a scaler value is desired. Therefore, the lead is implanted and the sensing thresholds are measured. The lead is moved in some indeterminate fashion and the sensing thresholds are again measured. The lead is continued to be repositioned until the sensing thresholds are optimized. Notice that the optimization desired results in a scaler output.

If one were to place electrode pairs along X axis 10, Y axis 12 and Z axis 14 one could readily measure not only the scaler value of the current flow, but could also readily determine its direction. So long as the three electrode pairs implanted are mutually orthogonal, such vector sensing can occur.

Studies have shown that this vector sensing is extremely important to early detection of certain arrhythmias. Using this technique, for example, the shift from one focus to another can readily be determined even though the depolarization currents are of the same scaler value.

The FIG. 2 is a plan view of a body implantable lead employing the present invention. The very distal end of body implantable lead 30 has electrode 32 affixed thereto. Proximal electrode 42, along with distal electrode 32, represent an electrode pair which sense currents parallel to the direction of lead body 30. Electrodes 34 and 36 comprise an electrode pair which measure currents in the illustrated direction. Electrode 38 is one electrode of an electrode pair. The other corresponding electrode is electrode 40 which is located 180° from electrode 38 and therefore is not shown in this view.

Each of the six electrodes (i.e. electrodes 32, 34, 36, 38, 40 and 42) is connected to a corresponding different one of six mutually insulated conductors which run the length of body implantable lead 30. Outer sheath 62 is of an insulating material which covers the six mutually insulated conductors about the length of body implantable lead 30.

A six-pole in-line electrical connector is located at the distal end of body implantable lead 30. Sealing rings 44, 46 and 48 are located distal to this six-pole, in-line connector. The connector itself consists of electrical contact areas 50, 52, 54, 56, 58 and 60. These electrical contact areas are metallic in nature and of a standard design. These are arranged to contact different ones of six corresponding terminal blocks within the implantable pulse generator.

FIG. 3 is a view of the six conductors of body implantable lead 30 with sheath 62 removed. Notice that the six mutually insulated conductors 64, 66, 68, 70, 72 and 74 are wrapped in multifilar (i.e. sixfilar) fashion. Conductor 64 conducts signals from electrode 42 to connector surface 60. (See also FIG. 2.) In similar fashion, conductors 66 and 68 conduct signals between electrodes 38 and 40 to connector surfaces 56 and 58, respectively. Conductors 70 and 72 conduct current from electrodes 34 and 36 to connector surfaces 52 and 54. And finally, conductor 74 conducts signals from distal electrode 32 to connector surface 50. The sixfilar, multipolar conductor shown in FIG. 3 is preferred because it allows for minimization of the cross sectional area of the lead notwithstanding the necessity to have six mutually insulated conductors. To present the desired low resistance to the transfer of current through these conductors it is recommended that drawn brazed strand construction of each conductor be employed. The inner matrix is silver in the preferred embodiment. Each of the conductors (i.e. conductor 64, 66, 68, 70, 72 and 74) is separately insulated using the body compatible insulating material such as urethane, silicone rubber, or other suitable material.

FIG. 4 is a cross sectional view of the distal end of body implantable lead 30. As can be seen in the figure, conductor 64 is coupled to electrode 42 at point 86. This electrical coupling may be through the use of welding or other known techniques.

Electrodes 38 and 40 are not shown in this view. However, it can be seen that conductors 66 and 68 leave the multifilar coil at the proper points. Electrodes 34 and 36 are shown being connected to conductors 70 and 72, respectively. These connection points are shown at 82 and 84 and again may be welded or coupled in other suitable fashion. Conductor 74 is shown as coupled to distal electrode 32 at point 80.

FIG. 5 shows a cross sectional view of the lead with electrodes 38 and 40 shown. Notice that conductors 66 and 68 are electrically coupled to electrodes 38 and 40 as shown. Again, connections at 88 and 90 may be welded or may use other suitable coupling techniques.

As thus seen the present invention may be embodied in a single, cylindrically shaped, body implantable lead having three mutually orthogonal pairs of electrodes. Those of ordinary skill in the art will be readily able to adapt the teachings herein to other configurations for the sensing and stimulation of electromuscular activity.

What is claimed is:

1. A body implantable lead comprising:
   first, second, third, fourth, fifth, and sixth electrodes mutually insulated from one another and arranged as three electrode pairs;
   an elongated lead body means for disposing said first, second, third, fourth, fifth, and sixth electrodes in substantially fixed relationship to one another, arranged such that said three electrode pairs define three mutually orthogonal sensing vectors;
   first, second, third, fourth, fifth, and sixth connector means for simultaneously coupling said first, second, third, fourth, fifth, and sixth electrodes to a monitoring device; and
   first, second, third, fourth, fifth, and sixth mutually insulated conductors extending along said lead body means each having a proximal end respectively coupled to said first, second, third, fourth, fifth, and sixth connector means and a distal end respectively coupled to said first, second, third, fourth, fifth, and sixth electrodes.

2. A body implantable lead according to claim 1 further comprising:
   an outer sheath covering said first, second, third, fourth, fifth, and sixth mutually insulated conductors.

3. A body implantable lead according to claim 2 wherein said first, second, third, fourth, fifth, and sixth mutually insulated conductors are arranged as a closely wound mulitifilar and mulitpolar coil.

4. A body implantable lead according to claim 3 wherein said first, second, third, fourth, fifth, and sixth connector means are arranged as an in-line connector assembly.

* * * * *